(12) United States Patent
Yamaguchi et al.

(10) Patent No.: US 11,110,109 B2
(45) Date of Patent: *Sep. 7, 2021

(54) WATER SOLUBLE O-GLYCOSYL FLAVONOID COMPOSITIONS AND METHODS FOR PREPARING SAME

(71) Applicant: Alps Pharmaceutical Ind. Co., Ltd., Gifu (JP)

(72) Inventors: Naoto Yamaguchi, Gifu (JP); Yui Sudaka, Gifu (JP); Mitsunori Ono, Lexington, MA (US)

(73) Assignee: ALPS Pharmaceutical Ind. Co., Ltd., Gifu (JP)

( * ) Notice: Subject to any disclaimer, the term of this patent is extended or adjusted under 35 U.S.C. 154(b) by 100 days.

This patent is subject to a terminal disclaimer.

(21) Appl. No.: 16/660,111

(22) Filed: Oct. 22, 2019

(65) Prior Publication Data

US 2021/0113599 A1 Apr. 22, 2021

(51) Int. Cl.
| | |
|---|---|
| *A61K 31/7048* | (2006.01) |
| *A61K 9/28* | (2006.01) |
| *A61K 47/10* | (2017.01) |
| *A61K 9/06* | (2006.01) |
| *A61K 9/08* | (2006.01) |
| *A61K 9/48* | (2006.01) |

(52) U.S. Cl.
CPC .......... *A61K 31/7048* (2013.01); *A61K 9/06* (2013.01); *A61K 9/08* (2013.01); *A61K 9/28* (2013.01); *A61K 9/4891* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 2,451,772 | A | 10/1948 | Plungian |
| 2,646,428 | A | 7/1953 | Chabrier |
| 2,975,168 | A | 3/1961 | Favre et al. |
| 4,285,964 | A | 8/1981 | Niebes et al. |
| 6,491,948 | B1 | 12/2002 | Buchholz et al. |
| 8,426,459 | B2 | 4/2013 | Stuchlik et al. |
| 2006/0099239 | A1 | 5/2006 | Coleman et al. |
| 2009/0082400 | A1 | 3/2009 | Lee et al. |
| 2009/0143317 | A1 | 6/2009 | Ono et al. |
| 2009/0149481 | A1 | 6/2009 | Azuma |
| 2009/0325906 | A1 | 12/2009 | Robbins et al. |
| 2010/0133373 | A1 | 6/2010 | Philips et al. |
| 2010/0204204 | A1 | 8/2010 | Zaworotko et al. |
| 2012/0083460 | A1 | 4/2012 | Emura et al. |
| 2014/0341934 | A1 | 11/2014 | Van Spronsen et al. |
| 2019/0060272 | A1 | 2/2019 | Aleksandrovich et al. |

FOREIGN PATENT DOCUMENTS

| | | |
|---|---|---|
| CN | 101301477 A | 11/2008 |
| DE | 2020/0800674 U1 | 10/2009 |
| EP | 0075626 A1 | 4/1983 |
| EP | 1669462 A1 | 6/2006 |
| GB | 2198041 A | 6/1988 |
| JP | S59232054 A | 12/1984 |
| JP | 6176552 A | 4/1986 |
| JP | H0654664 A | 3/1994 |
| JP | 2003/171274 A | 6/2003 |
| JP | 2005/198642 A | 7/2005 |
| JP | 2007/325588 A | 12/2007 |
| JP | 2008/092869 A | 4/2008 |
| JP | 2010/126503 A | 6/2010 |
| JP | 2010/248148 A | 11/2010 |
| JP | 2926411 B2 | 7/2011 |
| JP | WO2010/110328 A1 | 10/2012 |
| JP | 2015/181399 A | 10/2015 |
| JP | 2015208241 A | 11/2015 |
| JP | 2017/131215 A | 6/2017 |
| JP | 2019/024500 A | 2/2019 |
| RU | 2545905 C1 | 4/2015 |
| WO | WO-0012085 A1 | 3/2000 |
| WO | WO-2005030975 A1 | 4/2005 |
| WO | WO-2007114304 A1 | 10/2007 |
| WO | WO-2010/029913 A1 | 3/2010 |
| WO | WO-2010110328 A1 | 9/2010 |
| WO | WO-2011/104667 A1 | 9/2011 |
| WO | WO-2019/208574 A1 | 10/2019 |
| WO | WO-2019208574 A1 | 10/2019 |
| WO | WO-2019/230013 A1 | 12/2019 |

OTHER PUBLICATIONS

Acquaviva et al "Beneficial Effects of Rutin and L-Arginine Coadministration in a Rat Model of Liver Ischemia-Repeclusion Injury" American Journal of Physiology: Gastrointestinal and Liver Physiology vol. 296, pp. G664-G670, 2009.

Çelik et al "Antioxidant Capacity of Quercetin and its Glycosides in the Presence of β-Cyclodextrins: Influence of Glycosylation on Inclusion Complexation" Journal of Inclusion Phenomena and Macrocyclic Chemistry Bol, 83, pp. 309-319, 2015.

Hollman "Determinants of the Absorption of the Dietary Flavonoid Quercetin in Man" State Institute for Quality Control of Agricultural Products, 1997.

Vrijsen et al "Antiviral Activity of Flavones and Potentiation by Ascorbate" Journal of General Virology vol. 69, pp. 1749-1751, 1988.

(Continued)

*Primary Examiner* — Dale R Miller
(74) *Attorney, Agent, or Firm* — Cesari & McKenna, LLP

(57) ABSTRACT

A water-soluble composition including an O-glycosyl flavonoid compound, L-arginine, a sugar alcohol, and ascorbic acid or an alkali salt of ascorbic acid. The O-glycosyl flavonoid compound is rutin, isoquercitrin, or hesperidin, and a molar ratio between the O-glycosyl flavonoid compound and the sugar alcohol is 1:4.0-12.0. Also provided is a method for making the above-described water-soluble composition by combining the O-glycosyl flavonoid compound, L-arginine, the sugar alcohol, and ascorbic acid or an alkali salt thereof to form a mixture, and heating it at 110° C.-140° C. to melt the mixture.

12 Claims, No Drawings

(56) References Cited

OTHER PUBLICATIONS

Yamasaki et al "Flavonoid-Peroxidase Reaction as a Detoxification Mechanism of Plant Cells Against $H_2O_2$" Plant Physiology vol. 115, pp. 1405-1412, 1997.
Hamad et al "Metabolic Analysis of Various Date Palm Fruit (*Phoenix Dactylifera* L.) Cultivars from Saudi Arabia to Assess Their Nutritional Quality" Molecules vol. 20, pp. 13620-13641, 2015.
Abdelkader et al "Investigation into the Emerging Role of the Basic Amino Acid L-Lysine in Enhancing Solubility and Permeability of BCS Class II and BCS Class IV Drugs" Pharm Res vol. 35, pp. 1-18, 2018.
Gee et al "Intestinal Transport of Quercetin Glycosides in Rats Involves Both Deglycosylaton and Interaction with the Hexose Transport Pathway" The Journal of Nutrition vol. 130, pp. 2765-2771, 2000.

WATER SOLUBLE O-GLYCOSYL FLAVONOID COMPOSITIONS AND METHODS FOR PREPARING SAME

BACKGROUND

Several methods have been employed to improve the water solubility of natural flavonoids, e.g., O-glycosyl flavonoids. One approach is to make a solution of the flavonoid with a basic amino acid. Yet, the amount of basic amino acid required to maintain high water solubility of the flavonoid raises the pH of the solution to the point that the flavonoid becomes unstable and degrades over time.

There is still a need to develop water-soluble O-glycosyl flavonoid compositions having improved stability, increased solubility, and higher oral absorption of the flavonoid, as compared to existing compositions.

SUMMARY

A water-soluble composition is provided to meet the need set forth above. The composition includes an O-glycosyl flavonoid compound, L-arginine, a sugar alcohol, and ascorbic acid or an alkali salt of ascorbic acid. The O-glycosyl flavonoid compound is rutin, isoquercitrin, or hesperidin, and a molar ratio between the O-glycosyl flavonoid compound and the sugar alcohol is 1:4.0-12.0.

Also disclosed is a method for making the above-described water-soluble composition. The method is carried out by combining the O-glycosyl flavonoid compound, L-arginine, the sugar alcohol, and ascorbic acid or an alkali salt thereof to form a mixture, and heating the mixture at 110° C.-140° C. for a time sufficient to melt the mixture.

The details of one or more embodiments of the invention are set forth in the drawings and description below. Other features, objects, and advantages of the invention will be apparent from the description and from the claims. All references cited herein are hereby incorporated by reference in their entirety.

DETAILED DESCRIPTION

As summarized above, a water-soluble composition is disclosed herein that contains an O-glycosyl flavonoid, L-arginine, a sugar alcohol, and ascorbic acid or an ascorbic acid alkali salt.

The O-glycosyl flavonoid can be rutin, hesperidin, or isoquercitrin, and the sugar alcohol can be, but is not limited to maltitol, erythritol, xylitol, and sorbitol. The molar ratio between the O-glycosyl flavonoid and the sugar alcohol is 1:4.0-12.0. In a particular composition, the O-glycosyl flavonoid to sugar alcohol molar ratio is 1:4.0-8.0.

In the water-soluble composition, the molar ratio between the O-glycosyl flavonoid compound and L-arginine is 1:0.5-2.0. In an exemplary composition, this ratio is 1:0.7-1.5.

As mentioned above, the water-soluble composition also includes ascorbic acid or an alkali salt of ascorbic acid. The alkali salt can be a sodium salt or a potassium salt. In a particular composition, the alkali salt is a sodium salt. The molar ratio between the O-glycosyl flavonoid compound and the ascorbic acid or alkali salt is 1:0.02-0.5. In one composition, the ratio is 1:0.1-0.5.

Certain components of the above composition, e.g., rutin, isoquercitrin, hesperidin, and L-arginine, can exist in either an anhydrous form or a hydrate form (e.g., a mono-, di-, or tri-hydrate form) When a component is used in a hydrate form, the water in the hydrate form is included in its molecular weight for calculation of molar ratios.

In the water-soluble composition described, supra, the O-glycosyl flavonoid is typically present in a content of 10 wt % or higher (e.g., 20 wt % or higher, 30 wt % or higher, and 50 wt % or higher).

The water-soluble composition can also include a water soluble vitamin, e.g., vitamin B1, vitamin B3, vitamin B6, vitamin B9, or vitamin B12, in addition to the O-glycosyl flavonoid, L-arginine, sugar alcohol, and the ascorbic acid/alkali salt of ascorbic acid. The molar ratio of the O-glycosyl flavonoid to each water soluble vitamin in the composition can be 1:0.01-0.1.

The water-soluble composition, either a solid form or an aqueous form, can be in varied formulations for pharmaceutical, medical, or cosmetic use.

In one embodiment, the composition is in an oral formulation, e.g., a liquid, a capsule, a tablet, a pill, and a gel. An exemplary composition is in a capsule or a tablet, each formed with an enteric coating. The composition can further contain a pharmaceutically active agent, a pharmaceutically acceptable excipient, or a combination thereof. This embodiment includes a composition that is a pharmaceutical drug, a dietary supplement, a natural health product, a cosmetic product, a food product, or a beverage.

In another embodiment, the composition is in a topical formulation, e.g., one of a solution, a liniment, a lotion, a cream, an ointment, a paste, a gel, and an emulgel. The topical formulation can further contain a pharmaceutically active agent, a topically acceptable excipient, or a combination thereof. This embodiment includes a composition that is a cosmetic product, a skin care product, or a pharmaceutical drug.

An exemplary composition encompassed by the invention includes the O-glycosyl flavonoid, L-arginine, the sugar alcohol, and ascorbic acid or an ascorbic acid alkali salt as the only active ingredients. In another example, the composition includes the O-glycosyl flavonoid, L-arginine, the sugar alcohol, the ascorbic acid or an ascorbic acid alkali salt, and the water-soluble vitamin as the only active ingredients. Another composition consists essentially of or consists of the O-glycosyl flavonoid, L-arginine, the sugar alcohol, and ascorbic acid or an ascorbic acid alkali salt. A further composition consists essentially of or consists of the O-glycosyl flavonoid, L-arginine, the sugar alcohol, ascorbic acid or an ascorbic acid alkali salt, and the water-soluble vitamin. The composition of the invention is free of a solubility enhancer, e.g., a cyclodextrin.

A method for producing the water-soluble O-glycosyl flavonoid composition is also summarized above. The method is carried out by combining solid forms of an O-glycosyl flavonoid compound (e.g., rutin, isoquercitrin, and hesperidin), L-arginine, a sugar alcohol (e.g., maltitol, erythritol, xylitol, and sorbitol), and ascorbic acid or an alkali salt thereof to form a mixture, and heating the mixture at 110° C.-140° C. for a time sufficient to melt the mixture. The heating time can be 10 min. to 60 min. (e.g., 10, 15, 20, 25, 30, 35, 40, 45, 50, 55, and 60 min.).

In the above method, the molar ratio between the O-glycosyl flavonoid compound, the L-arginine, the sugar alcohol, and the ascorbic acid or the alkali salt thereof is 1:0.5-2.0:4.0-12.0:0.02-0.5. In particular methods the molar ratio is 1:0.7-1.5:4.0-8.0:0.1-0.5.

Disclosed herein is a correlation between the melting point of certain O-glycosyl flavonoids and their solubilities. The lower the melting point, the higher the solubility.

During the production method, the water-soluble O-glycosyl flavonoid compositions can undergo a browning process during production. Not to be bound by theory, it is believed that the browning is caused by caramelization of the sugar alcohol, a Maillard reaction, or other oxidation reactions. It has been discovered, surprisingly, that browning of the O-glycosyl flavonoid compositions at the temperatures employed to melt the O-glycosyl flavonoid can be retarded or prevented by addition of ascorbic acid or an alkali salt of ascorbic acid.

As a result of the significant enhancement of water solubility, O-glycosyl flavonoid compositions encompassed by the invention will have superior pharmacokinetic profiles, e.g., oral and dermal absorption, thereby making them suitable for pharmaceutical, medical, or cosmetic use.

Without further elaboration, it is believed that one skilled in the art can, based on the description above, utilize the present invention to its fullest extent. The specific examples below are to be construed as merely illustrative, and not limitative of the remainder of the disclosure in any way whatsoever.

EXAMPLES

Example 1: Preparation of Rutin/Maltitol/L-Arginine Composition

An aqueous solution of L-arginine (786 mg) and maltitol (3.0 g) in 17 ml was prepared and added to 50 ml of 99.5% ethanol containing 3 g of rutin. The mixture was stirred for 10 min., evaporated, and dried at 60° C. for 24 h to yield a powder. An amount of dried powder (226 mg containing 100 mg rutin) was added to 10 ml distilled $H_2O$ and mixed by vortexing for 30 s at which time the mixture was completely dissolved. The sample was passed through a 0.45 μm filter and the rutin concentration in the filtrate measured by HPLC. The measured concentration of rutin was 9.6 mg/ml.

Example 2: Preparation of Isoquercitrin/Maltitol/L-Arginine Composition

An aqueous solution of L-arginine (1.08 g) and maltitol (3.0 g) in 17 ml was prepared and added to 50 ml of 99.5% ethanol containing 3 g of isoquercitrin. The mixture was stirred for 10 min., evaporated, and dried at 60° C. for 24 h to yield a powder. The dried powder (236 mg containing 100 mg isoquercitrin) was added to 10 ml distilled $H_2O$ and mixed by vortexing for 30 s until the mixture was completely dissolved. The sample was passed through a 0.45 μm filter and the isoquercitrin concentration in the filtrate measured by HPLC. The measured concentration of isoquercitrin was 9.7 mg/ml.

Example 3: Preparation of Composition of Rutin/Erythritol/Ascorbate/L-Arginine by Melting Rutin (1.0 g) was mixed with erythritol (1.0 g) and sodium ascorbate (60 mg) and ground in a mortar. L-arginine (52 mg to 520 mg) was then added and the mixture ground in the mortar again. The molar ratio of each mixture is shown in Table 1 below.

TABLE 1

Molar ratio of rutin/erythritol/sodium ascorbate/L-arginine in mixtures

| Mixture No. | Rutin:Erythritol:Na Ascorbate:L-Arginine (mol/mol) |
| --- | --- |
| 1-01 | 1:5.4:0.2:0 |
| 1-02 | 1:5.4:0.2:0.2 |
| 1-03 | 1:5.4:0.2:0.5 |
| 1-04 | 1:5.4:0.2:0.7 |
| 1-05 | 1:5.4:0.2:1.0 |
| 1-06 | 1:5.4:0.2:1.5 |
| 1-07 | 1:5.4:0.2:2.0 |

Each mixture was heated in an aluminum heater block at 125° C. for 30 min., at which time the solids in each mixture were melted to completion.

Example 4: Preparation of Composition of Isoquercitrin/Erythritol/Ascorbate/L-Arginine by Melting Isoquercitrin (1.0 g) was mixed with erythritol (1.5 g) and sodium ascorbate (82 mg) and ground in a mortar. L-arginine (72 mg to 720 mg) was then added and the mixture ground in the mortar again. The molar ratio of each mixture is shown in Table 2 below.

TABLE 2

Molar ratio of isoquercitrin/erythritol/sodium ascorbate/L-arginine in mixtures

| Mixture No. | Isoquercitrin:Erythritol:Na Ascorbate:L-Arginine (mol/mol) |
| --- | --- |
| 2-01 | 1:5.9:0.2:0 |
| 2-02 | 1:5.9:0.2:0.2 |
| 2-03 | 1:5.9:0.2:0.5 |
| 2-04 | 1:5.9:0.2:0.7 |
| 2-05 | 1:5.9:0.2:1.0 |
| 2-06 | 1:5.9:0.2:1.5 |
| 2-07 | 1:5.9:0.2:2.0 |

As described above in Example 3, each mixture was heated in an aluminum heater block at 125° C. for 30 min., at which time the solids in each mixture were melted to completion.

Example 5: Preparation of Composition of Hesperidin/Erythritol/Ascorbate/L-Arginine by Melting Hesperidin (1.0 g) was mixed with erythritol (1.0 g) and sodium ascorbate (160 mg) and ground in a mortar. L-arginine (55 mg to 550 mg) was then added and the mixture ground in the mortar again. The molar ratio of each mixture is shown in Table 3 below.

TABLE 3

Molar ratio of hesperidin/erythritol/sodium ascorbate/L-arginine in mixtures

| Mixture No. | Hesperidin:Erythritol:Na Ascorbate:L-Arginine (mol:mol) | Appearance After Heating |
| --- | --- | --- |
| 3-01 | 1:5.1:0.5:0 | not melted |
| 3-02 | 1:5.1:0.5:0.2 | not melted |
| 3-03 | 1:5.1:0.5:0.5 | partially melted |

TABLE 3-continued

Molar ratio of hesperidin/erythritol/sodium ascorbate/L-arginine in mixtures

| Mixture No. | Hesperidin:Erythritol:Na Ascorbate:L-Arginine (mol:mol) | Appearance After Heating |
|---|---|---|
| 3-04 | 1:5.1:0.5:0.7 | partially melted |
| 3-05 | 1:5.1:0.5:1.0 | completely melted |
| 3-06 | 1:5.1:0.5:1.5 | completely melted |
| 3-07 | 1:5.1:0.5:2.0 | completely melted |

Again, each mixture was heated in an aluminum heater block at 125° C. for 30 min. As shown in Table 3 above, complete melting of the solids was achieved when L-arginine was present in at least an equimolar ratio to hesperidin. See mixtures 3-05, 3-06, and 3-07.

Example 6: Solubility of Rutin Compositions

The seven rutin compositions prepared as described in Example 3 above (41.2 mg to 51.6 mg, each containing 20 mg rutin) were each added to a 2 ml aliquot of distilled $H_2O$, mixed by a vortex mixer for 30 s, and incubated for 24 h at room temperature. A control sample was prepared by mixing 20 mg rutin alone with 2 ml of distilled $H_2O$ (Control 1). A second control sample was prepared by mixing, in 2 ml distilled $H_2O$, rutin, erythritol, and Na ascorbate in the amounts shown for mixture 1-01 in Table 1 above. Each sample was passed through a 0.45 μm filter and the rutin concentration in the filtrate measured by HPLC. The results are shown below in Table 4.

TABLE 4

Rutin composition solubility

| Mixture No. | Rutin:Erythritol:Na Ascorbate:L-Arginine (mol:mol) | Concentration of Rutin in $H_2O$ (mg/mL) | Fold Increase in Rutin Solubility |
|---|---|---|---|
| Control 1 | 1:0:0:0 | 0.021 | — |
| Control 2 | 1:5.4:0.2:0 | 0.022 | 1.0 |
| 1-01 | 1:5.4:0.2:0 | 0.090 | 4 |
| 1-02 | 1:5.4:0.2:0.2 | 0.43 | 20 |
| 1-03 | 1:5.4:0.2:0.5 | 1.8 | 84 |
| 1-04 | 1:5.4:0.2:0.7 | 3.0 | 134 |
| 1-05 | 1:5.4:0.2:1.0 | 4.4 | 201 |
| 1-06 | 1:5.4:0.2:1.5 | 8.4 | 385 |
| 1-07 | 1:5.4:0.2:2.0 | >9.2 | >418 |

Unexpectedly, erythritol significantly maintained the high solubility of rutin even when the molar ratio of rutin to L-arginine was lowered. It was also surprising that mixture 1-01 showed a 4-fold increase in rutin solubility, as compared to Control 2 having the same composition. Mixture 1-01 was formed by melting the components together with heat, as described in Example 1 above, while the components of Control 2 were not heated prior to mixing with distilled $H_2O$. Clearly, melting is important for increasing rutin solubility in the mixture.

Example 7: Solubility of Isoquercitrin Compositions

The seven isoquercitrin compositions prepared as described in Example 4 (51.6 mg to 66.0 mg, each containing 2 mg isoquercitrin) were each added to a 2 ml aliquot of distilled $H_2O$, mixed by a vortex mixer for 30 s, and incubated for 24 h at room temperature. Controls 1 and 2 were prepared in the same manner as in Example 6 above. Each sample was passed through a 0.45 μm filter and the isoquercitrin concentration in the filtrate measured by HPLC. The results are shown below in Table 5.

TABLE 5

Isoquercitrin composition solubility

| Mixture No. | Isoquercitrin:Erythritol:Na Ascorbate:L-Arginine (mol:mol) | Concentration of Isoquercitrin in $H_2O$ (mg/mL) | Fold Increase in Isoquercitrin Solubility |
|---|---|---|---|
| Control 1 | 1:0:0:0 | 0.027 | — |
| Control 2 | 1:5.9:0.2:0 | 0.082 | 3.0 |
| 2-01 | 1:5.9:0.2:0 | 0.22 | 8.0 |
| 2-02 | 1:5.9:0.2:0.2 | 1.6 | 57 |
| 2-03 | 1:5.9:0.2:0.5 | 3.4 | 122 |
| 2-04 | 1:5.9:0.2:0.7 | 5.0 | 182 |
| 2-05 | 1:5.9:0.2:1.0 | 7.9 | 286 |
| 2-06 | 1:5.9:0.2:1.5 | >9.3 | >337 |
| 2-07 | 1:5.9:0.2:2.0 | >9.2 | >335 |

It was surprising that addition of erythritol maintained the increased solubility of isoquercitrin in the presence of L-arginine even as the molar ratio of isoquercitrin to L-arginine was reduced.

Example 8: Solubility of Hesperidin Compositions

The seven hesperidin compositions prepared as described in Example 5 (43.2 mg to 54.2 mg, each containing 2 mg hesperidin) were each added to a 2 ml aliquot of distilled $H_2O$, mixed by a vortex mixer for 30 s, and incubated for 24 h at room temperature. Controls 1 and 2 were prepared in the same manner as in Examples 6 and 7 above. Each sample was passed through a 0.45 μm filter and the hesperidin concentration in the filtrate measured by HPLC. The results are shown below in Table 6.

TABLE 6

Hesperidin composition solubility

| Mixture No. | Hesperidin:Erythritol:Na Ascorbate:L-Arginine (mol:mol) | Concentration of Hesperidin in $H_2O$ (mg/mL) | Fold Increase in Hesperidin Solubility |
|---|---|---|---|
| Control 1 | 1:0:0:0 | 0.024 | — |
| Control 2 | 1:5.1:0.5:0 | 0.023 | 1.0 |
| 3-01 | 1:5.1:0.5:0 | 0.014 | 0.6 |
| 3-02 | 1:5.1:0.5:0.2 | 0.28 | 12 |
| 3-03 | 1:5.1:0.5:0.5 | 1.2 | 48 |
| 3-04 | 1:5.1:0.5:0.7 | 1.6 | 67 |
| 3-05 | 1:5.1:0.5:1.0 | 2.5 | 102 |
| 3-06 | 1:5.1:0.5:1.5 | 3.2 | 130 |
| 3-07 | 1:5.1:0.5:2.0 | 4.4 | 182 |

Unexpectedly, the increased solubility of hesperidin resulting from L-arginine in the compositions is maintained by adding erythritol, even as the amount of L-arginine is reduced.

Example 9: Lowering of O-Glycosyl Flavonoid Compound Melting Point by Erythritol and L-Arginine Samples of rutin, isoquercitrin, and hesperidin with erythritol were prepared as described, infra, to determine melting temperature in the presence or absence of L-arginine.

Two samples of rutin (1 g each) were mixed with 0.7 g erythritol and ground in a mortar. L-arginine (0.26 g) was added to one of the two samples.

For isoquercitrin, two 1 g samples were ground in a mortar together with 1 g erythritol, and L-arginine (0.36 g) was added to one of the samples.

Hesperidin samples were prepared by grinding two 1 g samples with 1 g erythritol in a mortar and adding 0.52 g L-arginine to one sample.

All of the samples prepared as above were placed in an aluminum heating block, which was heated up to 170° C. The melting point of each sample was recorded. The results are presented below in Table 7.

TABLE 7

Melting point lowering effect of erythritol/L-arginine

| Mixture No. | Flavonoid | Flavonoid:Erythritol:L-Arginine (mol:mol) | Melting point (° C.) |
|---|---|---|---|
| 7-01 | Rutin | 1:3.8:0 | 140 |
| 7-02 | Rutin | 1:3.8:1.0 | 120 |
| 7-03 | Isoquercitrin | 1:4:0 | 170 |
| 7-04 | Isoquercitrin | 1:4:1.0 | 125 |
| 7-05 | Hesperidin | 1:5.1:0 | >170 |
| 7-06 | Hesperidin | 1:5.1:2.0 | 125 |

It is noteworthy that addition of erythritol significantly lowers the reported melting points of rutin (190° C.) and isoquercitrin (230° C.) by as much as 50° C. and 60° C. respectively. Lowering of the melting point of hesperidin (260° C.) by erythritol could not be measured under the experimental conditions used.

Addition of both erythritol and L-arginine was even more effective for lowering melting points. The results showed that the melting points of rutin, isoquercitrin, and hesperidin were lowered by at least 70° C. in the presence of both erythritol and L-arginine.

Example 10: Melting Point Lowering of Rutin by Sugar Alcohols

Samples of rutin (1.0 g), L-arginine (0.39 g) and Na ascorbate (60 mg) were combined and mixed separately with 1.5 g of erythritol, xylitol, sorbitol, maltitol, mannitol, or paratinitt. The mixtures were ground in a mortar and subjected to heat in an aluminum heating block. The melting temperatures were recorded and are shown below in Table 8.

TABLE 8

Rutin melting point

| Mixture No. | Sugar alcohol | Rutin:L-Arginine:Na Ascorbate:Sugar alcohol (mol:mol) | Melting point (° C.) |
|---|---|---|---|
| 8-01 | Erythritol | 1:1.5:0.2:8.2 | 126 |
| 8-02 | Xylitol | 1:1.5:0.2:6.6 | 126 |
| 8-03 | Sorbitol | 1:1.5:0.2:5.5 | 126 |
| 8-04 | Maltitol | 1:1.5:0.2:2.9 | 128 |
| 8-05 | Mannitol | 1:1.5:0.2:5.5 | Not melted at 138 |
| 8-06 | Paratinitt | 1:1.5:0.2:2.9 | 138 |
| 8-07 | Erythritol | 1:1.5:0.2:3.8 | 126 |
| 8-08 | Erythritol | 1:1.5:0.2:2.7 | 126 |

It is noted that xylitol, maltitol and sorbitol, like erythritol described in Example 9, also lowered the melting point of rutin (190° C.) by approximately 60 degrees. This melting point lowering was significant, as compared to similar sugar alcohols, i.e., mannitol and paratinitt.

Example 11: Ascorbic Acid Prevents Browning of Rutin

Varying amounts of Na ascorbate were mixed with rutin (1.0 g), L-arginine (1.0 g) and erythritol (1.0 g). Each mixture was ground in a mortar and heated in an aluminum heating block at 122° C. for 15 min. The heated mixtures were each added to an aliquot of distilled $H_2O$ to obtain a rutin concentration of 1% (w/v). The samples were filtered through a 0.45 μm membrane filter. Each filtrate (300 μL) was further diluted with distilled water (2.7 mL) and then the absorbance at 550 nm was measured immediately and 24 h later to detect browning of the rutin solutions. The absorbance difference ($\Delta A_{550nm}$) of each sample between time 0 and 24 h are shown in Table 9 below.

TABLE 9

Prevention of rutin browning reaction

| Mixture No. | Rutin:Erythritol:Arginine:Na Ascorbate (mol:mol) | $\Delta A_{550\,nm}$ |
|---|---|---|
| 9-01 | 1:3.8:1:0 | 0.0154 |
| 9-02 | 1:3.8:1:0.1 | 0.0018 |
| 9-03 | 1:3.8:1:0.2 | 0.0026 |
| 9-04 | 1:3.8:1:0.5 | 0.0035 |
| 9-05 | 1:3.8:1:1 | 0.0033 |
| 9-06 | 1:3.8:1:1.5 | 0.0038 |
| 9-07 | 1:3.8:1:2 | 0.0031 |
| 9-08 | 1:3.8:1:3 | 0.0020 |

The results showed that sodium ascorbate significantly reduced the browning reaction of rutin compositions by as much as 8.5-fold.

Example 12: Ascorbic Acid Prevents Browning of Isoquercitrin

Varying amounts of Na ascorbate were mixed with isoquercitrin (1.0 g), L-arginine (1.0 g) and erythritol (1.5 g). Each mixture was ground in a mortar and heated in an aluminum heating block at 126° C. for 15 min. The heated mixtures were each added to an aliquot of distilled $H_2O$ to obtain an isoquercitrin concentration of 1% (w/v). The samples were filtered through a 0.45 μm membrane filter. Each filtrate (300 μL) was further diluted with distilled water (2.7 mL) and then the absorbance at 550 nm was measured immediately and 24 h later to detect browning of the rutin solutions. The absorbance difference ($\Delta A_{550nm}$.) of each sample between time 0 and 24 h are shown in Table 10 below.

TABLE 10

Prevention of isoquercitrin browning reaction

| Mixture No. | Isoquercitrin:Erythritol:Arginine:Na Ascorbate (mol:mol) | $\Delta A_{550\,nm}$ |
|---|---|---|
| 10-01 | 1:4:1:0 | 0.0219 |
| 10-02 | 1:4:1:0.1 | 0.0060 |
| 10-03 | 1:4:1:0.2 | 0.0023 |
| 10-04 | 1:4:1:0.5 | 0.0042 |
| 10-05 | 1:4:1:1 | 0.0079 |
| 10-06 | 1:4:1:1.5 | 0.0041 |

TABLE 10-continued

Prevention of isoquercitrin browning reaction

| Mixture No. | Isoquercitrin:Erythritol:Arginine:Na Ascorbate (mol:mol) | $\Delta A_{550\ nm}$ |
|---|---|---|
| 10-07 | 1:4:1:2 | 0.0058 |
| 10-08 | 1:4:1:3 | 0.0087 |

Sodium ascorbate reduced the browning reaction of isoquercitrin compositions by as much as 9.5-fold.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A water-soluble composition comprising an O-glycosyl flavonoid compound, L-arginine, a sugar alcohol, and an alkali salt of ascorbic acid, wherein the O-glycosyl flavonoid compound is selected from the group consisting of rutin, isoquercitrin, and hesperidin, the sugar alcohol is selected from the group consisting of maltitol, erythritol, xylitol, and sorbitol, the molar ratio between the O-glycosyl flavonoid compound and the L-arginine is 1:0.5-2.0 and the molar ratio between the glycosyl compound and the sugar alcohol is 1:4.0-12.0.

2. The water-soluble composition of claim 1, wherein the molar ratio between the O-glycosyl flavonoid compound and the sugar alcohol is 1:4.0-8.0.

3. The water-soluble composition of claim 1, wherein the molar ratio between the O-glycosyl flavonoid compound and the L-arginine is 1:0.7-1.5.

4. The water-soluble composition of claim 1, wherein the molar ratio between the O-glycosyl flavonoid compound and the alkali salt of ascorbic acid is 1:0.02-0.5.

5. The water-soluble composition of claim 4, wherein the molar ratio between the O-glycosyl flavonoid compound and the alkali salt of ascorbic acid is 1:0.1-0.5.

6. The water-soluble composition of claim 1, further comprising vitamin B1, vitamin B3, vitamin B6, vitamin B9, or vitamin B12.

7. The water-soluble composition of claim 1, wherein the composition is a pharmaceutical drug, a dietary supplement, a natural health product, a cosmetic product, a food product, or a beverage.

8. The water-soluble composition of claim 7, wherein the composition is an oral formulation selected from the group consisting of a liquid, a capsule, a tablet, a pill, and a gel.

9. The water-soluble composition of claim 8, wherein the composition is in a capsule or a tablet, each formed with an enteric coating.

10. The water-soluble composition of claim 7, wherein the composition is in a topical formulation selected from the group consisting of a solution, a liniment, a lotion, a cream, an ointment, a paste, a gel, and an emulgel.

11. The water-soluble composition of claim 10, wherein the composition is a cosmetic product, a skin care product, or a pharmaceutical drug.

12. A method for producing a water-soluble O-glycosyl flavonoid composition, the method comprising combining an O-glycosyl flavonoid compound, L-arginine, a sugar alcohol, and an alkali salt of ascorbic acid to form a mixture, and heating the mixture at 110° C.-140° C. for a time sufficient to melt the mixture, wherein the O-glycosyl flavonoid compound, the L-arginine, the sugar alcohol, and the alkali salt of ascorbic acid are each in solid form; the O-glycosyl flavonoid compound is selected from the group consisting of rutin, isoquercitrin, and hesperidin, the sugar alcohol is selected from the group consisting of maltitol, compound and the L-arginine is 1:0.5-2.0, and the molar ratio between the O-glycosyl flavonoid compound and the sugar alcohol is 1:4.0-12.0.

* * * * *

UNITED STATES PATENT AND TRADEMARK OFFICE
CERTIFICATE OF CORRECTION

| | |
|---|---|
| PATENT NO. | : 11,110,109 B2 |
| APPLICATION NO. | : 16/660111 |
| DATED | : September 7, 2021 |
| INVENTOR(S) | : Naoto Yamaguchi et al. |

It is certified that error appears in the above-identified patent and that said Letters Patent is hereby corrected as shown below:

In the Claims

Column 10, Claim 12 should read as follows:
12. A method for producing a water-soluble O-glycosyl flavonoid composition, the method comprising combining an O-glycosyl flavonoid compound, L-arginine, a sugar alcohol, and an alkali salt of ascorbic acid to form a mixture, and heating the mixture at 110° C.-140° C. for a time sufficient to melt the mixture, wherein the O-glycosyl flavonoid compound, the L-arginine, the sugar alcohol, and the alkali salt of ascorbic acid are each in solid form; the O-glycosyl flavonoid compound is selected from the group consisting of rutin, isoquercitrin, and hesperidin, the sugar alcohol is selected from the group consisting of maltitol, erythritol, xylitol, and sorbitol, the molar ratio between the O-glycosyl flavonoid compound and the L-arginine is 1:0.5-2.0, and the molar ratio between the O-glycosyl flavonoid compound and the sugar alcohol is 1:4.0-12.0.

Signed and Sealed this
Fourteenth Day of March, 2023

Katherine Kelly Vidal
*Director of the United States Patent and Trademark Office*